United States Patent
Crandell et al.

(10) Patent No.: US 12,178,769 B2
(45) Date of Patent: Dec. 31, 2024

(54) ADJUSTABLE HOSPITAL BED FOR LATERALLY POSITIONING A PATIENT AND RELATED METHODS

(71) Applicant: LIFE CONCEPTS, INC., Orlando, FL (US)

(72) Inventors: James Crandell, Orlando, FL (US); Rolonda Carmichael, Orlando, FL (US); Robin Nielsen, Orlando, FL (US); Vivienne Pearson, Orlando, FL (US); Violet Bennett, Orlando, FL (US); Judy Fitzpatrick, Orlando, FL (US); Lovenia Brokenborough, Orlando, FL (US); Latonya Fair, Orlando, FL (US); Timothy Jones, Orlando, FL (US); John R. Gill, Orlando, FL (US); Erica Plazibat, Orlando, FL (US)

(73) Assignee: LIFE CONCEPTS, INC., Orlando, FL (US)

( * ) Notice: Subject to any disclaimer, the term of this patent is extended or adjusted under 35 U.S.C. 154(b) by 294 days.

(21) Appl. No.: 17/830,926

(22) Filed: Jun. 2, 2022

(65) Prior Publication Data
US 2023/0390132 A1 Dec. 7, 2023

(51) Int. Cl.
*A61G 7/005* (2006.01)
*A61G 7/018* (2006.01)

(52) U.S. Cl.
CPC ............. *A61G 7/005* (2013.01); *A61G 7/018* (2013.01)

(58) Field of Classification Search
CPC .......... A61G 7/005; A61G 7/018; A61G 7/07; A61G 7/103; A61G 7/1025; A61G 7/001;
(Continued)

(56) References Cited

U.S. PATENT DOCUMENTS

| 3,344,445 A | 3/1967 | Crawford |
| 3,884,225 A | 5/1975 | Witter |

(Continued)

FOREIGN PATENT DOCUMENTS

| EP | 2719365 | 4/2014 |
| FR | 2123807 | 9/1972 |

(Continued)

OTHER PUBLICATIONS

"Mortise." Vocabulary.com, Mortise Definition, www.vocabulary.com/dictionary/mortise (Year: 2020).*

(Continued)

*Primary Examiner* — Adam C Ortiz
*Assistant Examiner* — Madison Emanski
(74) *Attorney, Agent, or Firm* — ALLEN, DYER ET AL.

(57) ABSTRACT

An adjustable hospital bed for laterally positioning a patient includes a support frame having a top end and a bottom end, a plurality of wheels secured to the bottom end of the support frame, and a body pad having a head end and a foot end and a plurality of back pad mortises around its periphery. The bed also includes a back pad having a top edge, a bottom edge, and a plurality of back pad tenons that extend from the bottom edge and are removably inserted into the plurality of back pad mortises of the body pad to support the back pad on its bottom edge at an angle relative to the body pad. In addition, the bed includes a linear actuator configured to lift the head end of the body pad and a tilt adjustment mechanism configured to laterally tilt the body pad.

18 Claims, 5 Drawing Sheets

(58) Field of Classification Search
CPC .. A61G 7/008; A61G 13/122; A61G 13/1225; A61G 7/015; A61G 7/0573; A61G 7/0507; A61G 7/012; A61G 2200/32; A61G 2203/42; A61G 7/05769; A61G 7/0509; A61G 2203/12; A61G 5/006; A61G 7/0514; A61G 7/0513; A61F 5/3769; Y10S 5/942
USPC ........ 5/81.1 R, 608, 607, 42, 185, 430, 617, 5/510, 618, 600, 613, 425, 715, 615, 621, 5/622, 632, 710, 424, 428, 601, 628, 629, 5/713, 83.1, 610, 611, 612, 614, 616, 5/624, 625, 627, 630, 637, 609
See application file for complete search history.

(56) References Cited

U.S. PATENT DOCUMENTS

| | | | |
|---|---|---|---|
| 3,900,906 | A | 8/1975 | Berthelsen |
| 4,934,002 | A | 6/1990 | Watanabe |
| 5,502,853 | A * | 4/1996 | Singleton ............. A61G 7/0507 5/430 |
| 6,154,900 | A | 12/2000 | Shaw |
| 6,253,402 | B1 | 7/2001 | Lin |
| 7,024,711 | B1 * | 4/2006 | Stasney .................... A61B 8/40 5/601 |
| 7,080,422 | B2 | 7/2006 | Ben-Levi |
| 7,441,293 | B1 | 10/2008 | Singer et al. |
| 7,562,403 | B2 | 7/2009 | Wei et al. |
| 8,561,226 | B1 | 10/2013 | Barr et al. |
| 10,314,754 | B2 | 6/2019 | Karwal et al. |
| 2003/0115673 | A1 | 6/2003 | Hand et al. |
| 2006/0085913 | A1 * | 4/2006 | Kawakami ........... A47C 20/041 5/624 |
| 2009/0089930 | A1 | 4/2009 | Benzo |
| 2015/0047120 | A1 * | 2/2015 | Partridge ................ A61G 7/001 53/396 |
| 2019/0117483 | A1 * | 4/2019 | Tessmer ............... A61G 7/0507 |

FOREIGN PATENT DOCUMENTS

| | | | | |
|---|---|---|---|---|
| WO | WO-0160308 A2 * | 8/2001 | ........ A61G 1/0225 |
| WO | WO-02058617 A2 * | 8/2002 | ............ A61B 6/0487 |
| WO | WO2004016136 | 2/2004 | |

OTHER PUBLICATIONS

"Pad." Cambridge Dicitonary, Pad Definition, https://dictionary.cambridge.org/us/dictionary/english/pad (Year: 2019).*

* cited by examiner

ADJUSTABLE HOSPITAL BED FOR LATERALLY POSITIONING A PATIENT AND RELATED METHODS

FIELD OF THE INVENTION

The present invention relates to the field of hospital beds, and, more particularly, to an adjustable hospital bed for laterally positioning a patient and related methods.

BACKGROUND

Many people unfortunately suffer from health disorders that affects movement and muscle tone or posture. Accordingly, people with these types of disorders can have impaired movement and may have a reduced range of motion at various joints due to muscle stiffness. In particular, it is often beneficial for them to lay on their side to help improve comfort and their well-being.

There have been previous attempts to fabricate a side lying type bed that supports the patient on their side rather than on their back. This helps to alleviate pressure ulcers, thrombosis, and respiratory complications, among other things. The existing side lying type beds are typically cumbersome to move or are stationary, and are otherwise inadequate to serve the needs of the patient that is non-ambulatory.

Accordingly, there is a need in the art for an improved hospital bed that supports and laterally secures a patient on their side comfortably and that is also maneuverable within a medical or assisted living facility.

SUMMARY

An adjustable hospital bed for laterally positioning a patient is disclosed. The adjustable hospital bed includes a support frame having a top end and a bottom end, and a plurality of wheels secured to the bottom end of the support frame, where the support frame comprises a lower platform, an upper platform, and a plurality of vertical supports therebetween. The bed also includes a body pad having a head end and a foot end and a plurality of back pad mortises around its periphery. The body pad is adjustably secured to the top end of the support frame. The bed also includes a back pad having a top edge, a bottom edge, and a plurality of back pad tenons extending from the bottom edge and that are removably inserted into the plurality of back pad mortises of the body pad to support the back pad on its bottom edge at an angle relative to the body pad. A back pad locking rod is configured to removable secure the back pad tenons to the back pad mortises by sliding the back pad locking rod therethrough and the plurality of back pad tenons comprise a plurality of position apertures configured to receive the back pad locking rod therethrough and to secure the back pad at the desired angle relative to the body pad.

In addition, the bed includes a linear actuator having a first end secured to the top end of the support frame and a second end secured to an underside of the body pad, where the linear actuator is configured to lift the head end of the body pad. The support frame may have a power supply in electrical communication with the linear actuator.

The bed includes a tilt adjustment mechanism having a first portion secured to the top end of the support frame and a second overlapping portion in communication with an underside of the body pad, where the second overlapping portion of the tilt adjustment mechanism is configured to rotate relative to the first portion to laterally tilt the body pad relative to a front or rear of the support frame. The tilt adjustment mechanism has a handle and a plurality of adjustment holes cooperating to secure the body pad at a desired tilting angle relative to the support frame.

The bed may also include an upper push handle and a lower push handle, where the upper push handle is secured to the body pad, and the lower push handle is secured to the support frame. A rear surface of the back pad may have at least one back pad handle secured thereto. In addition, the bed may have a foot pad extending from the foot end of the body pad, where the foot pad is configured to be rotated up and locked in alignment with the body pad or unlocked and rotated down.

The bed also includes a removable harness comprising a torso pad and at least one strap, where the torso pad is configured to be placed adjacent to a torso of the patient and the at least one strap slides around the back pad and body pad to secure the patient laterally on their side against the back pad.

In another particular aspect, a method of laterally positioning a patient using an adjustable hospital bed is disclosed. The adjustable hospital bed includes a support frame having a top end and a bottom end, and a body pad having a head end and a foot end and a plurality of back pad mortises around its periphery, where the body pad is adjustably secured to the top end of the support frame. A back pad having a plurality of back pad tenons extending from a bottom edge is removably inserted into the plurality of back pad mortises of the body pad to support the back pad on its bottom edge at an angle relative to the body pad, a linear actuator having a first end is secured to the top end of the support frame and a second end secured to an underside of the body pad, and a tilt adjustment mechanism is configured to rotate to laterally tilt the body pad relative to a front or rear of the support frame. The method includes positioning a patient on the body pad on their side, placing a torso pad adjacent to a torso of the patient, and sliding a strap that is attached to the torso pad around the back pad and body pad to secure the patient laterally on their side against the back pad. In addition, the method includes using the linear actuator and the tilt adjustment mechanism to secure the patient at the desired lateral position.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
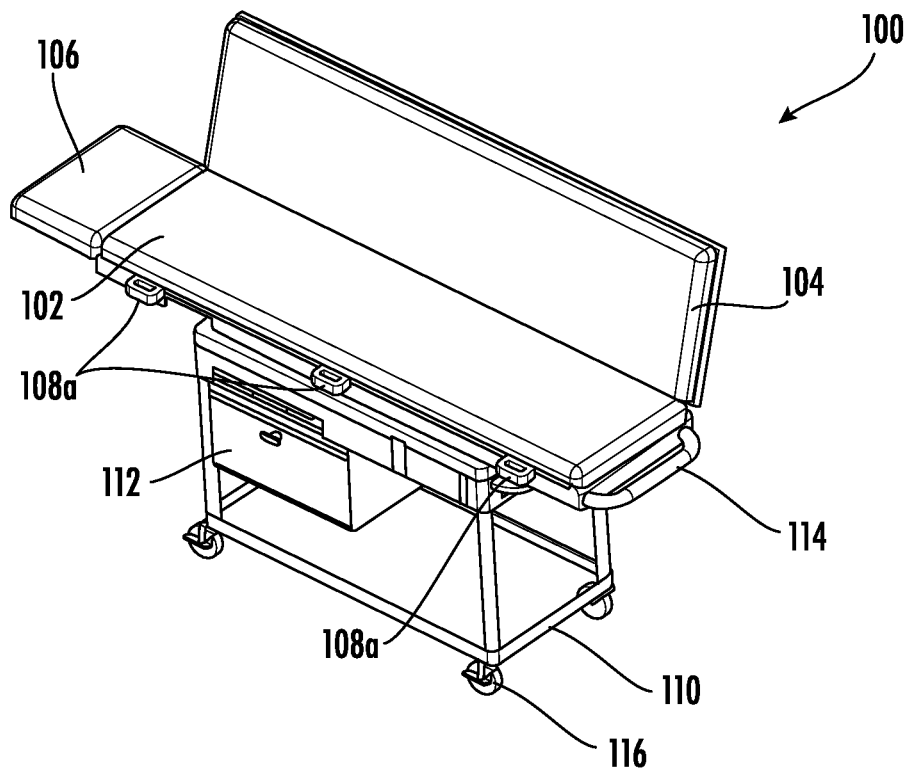
FIG. 1 is a perspective schematic view of an adjustable hospital bed for laterally positioning a patient in which various aspects of the disclosure may be implemented.

Referring now to FIG. 1, an adjustable hospital bed (the "bed") for laterally positioning a patient is illustrated, and generally designated 100. The bed 100 includes a body pad 102 that is for the patient to lie on. In particular, the body pad 102 is rectangular shaped and sized so that a patient can lay on their side. The bed 100 may also include an upper push handle 114 secured to the body pad 102.

A back pad 104 is secured along either side of the body pad 102 to create a vertical surface for the patient to support their back when laying on their side. The body pad 102 includes a head end which is the end where the patient lays their head, and a foot end on the opposing end where the patient places their feet. A foot pad 106 is at the end of the foot end that can be rotated up and locked in place to extend the length of the body pad 102. Likewise, the foot pad 106 can be rotated down and out of the way if not needed.

Figure 2:
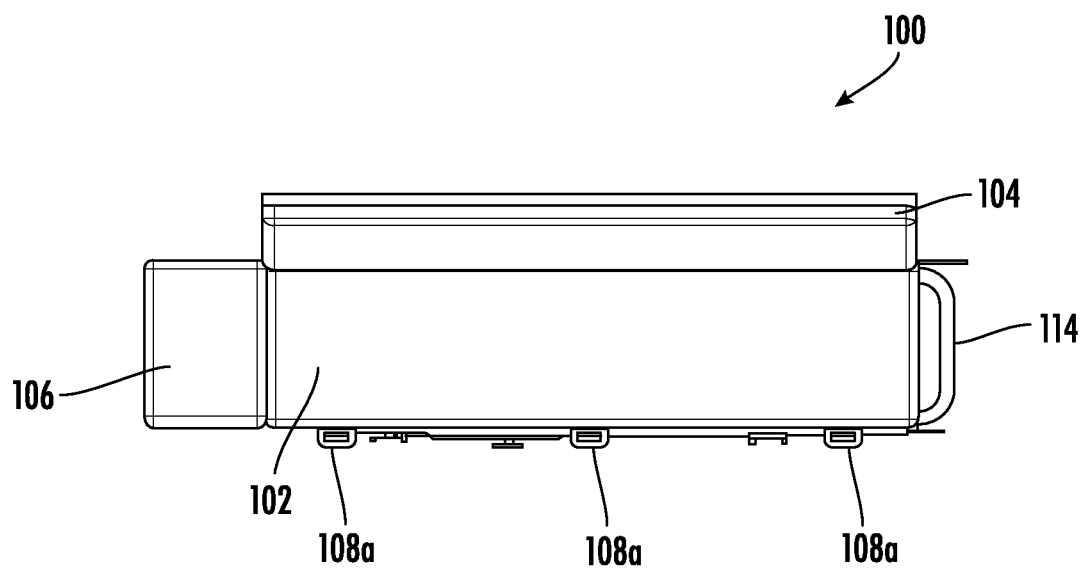
FIG. 2 is a top schematic view of the adjustable hospital bed of FIG. 1.

Still referring to FIG. 1, the back pad 104 is secured on the rear edge of the body pad 102 so that a patient can lie on their left side with their back against the back pad 104. The back pad 104 is secured to the body pad 102 using mortises and tenons along a bottom edge of the back pad 104. As shown in FIGS. 1 and 2, a plurality of mortises 108a are shown along the front edge of the body pad 102. Similarly, the rear edge of the body pad 102 has similar mortises for receiving the tenons of the back pad 104. Thus, the back pad 104 can be removed from the rear edge of the body pad 102 and secured to the front edge of the body pad 102 so that the patient can lie on the right side. The mortise and tenon connection between the body pad 102 and the back pad 104 ensures a strong and firm structural connection to support the patient.

The body pad 102 is secured to a top of the support frame 110. The support frame 110 may generally be rectangular shape and roll on wheels 116. Accordingly, the bed 100 is mobile and can easily navigate hallways and other crowded spaces where space is limited in order to move patients. An upper push handle is secured proximate the head end of the bed 102 to facilitate pushing and turning the bed 100 when being moved.

Figure 3:
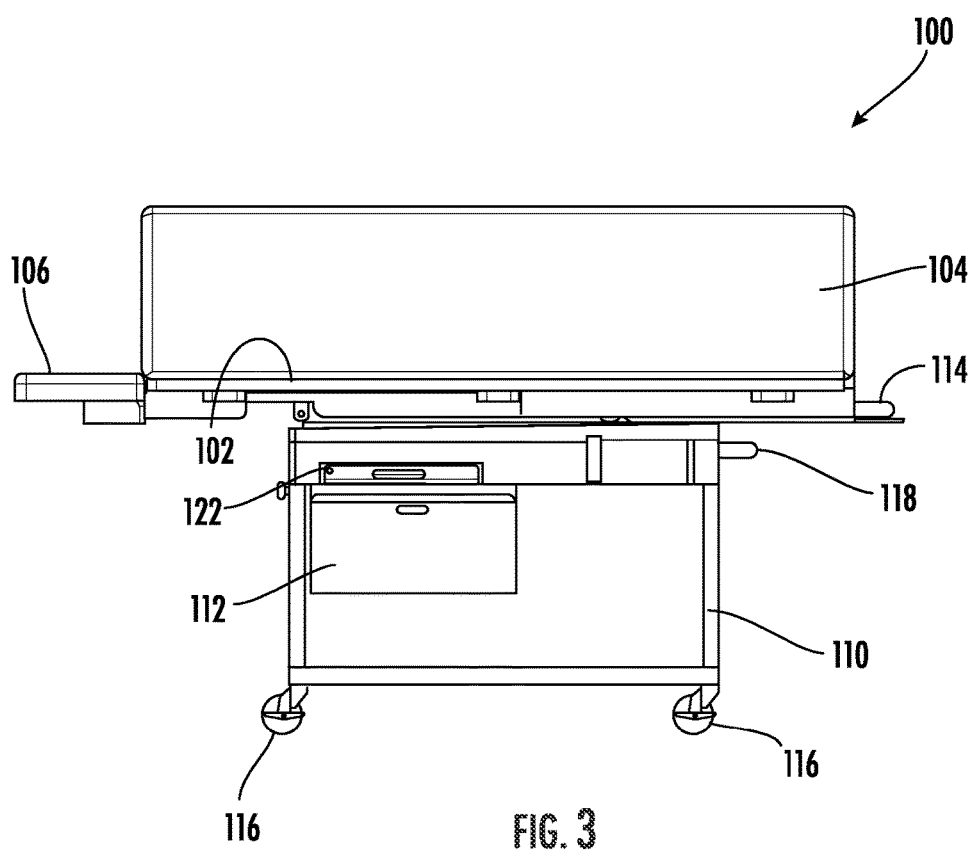
FIG. 3 is a front schematic view of the adjustable hospital bed of FIG. 1.

A view of the front of the bed 100 is illustrated in FIG. 3. A laptop tray 122 is positioned on the support frame 110 above the storage cabinet 112. The laptop tray 122 extends out from the support frame so that caregiver can place and work on a laptop as needed. The laptop tray 122 can be pushed back in when not needed and be stored away. In addition, a lower push handle 118 is located on the support frame 110 and can be used when the body pad 104 is tilted up as explained below.

Figure 4:
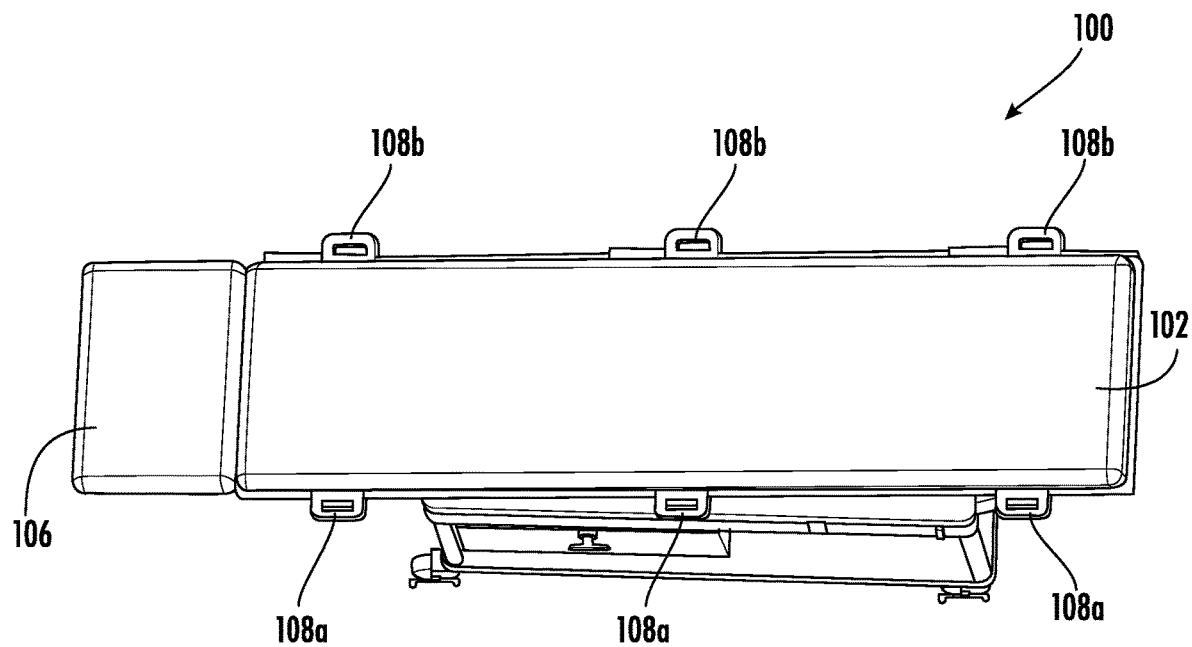
FIG. 4 is a top schematic view of the hospital bed of FIG. 1 shown without a back pad.

Referring now to FIG. 4, a top view of the bed 100 without the back pad 104 is shown. A plurality of mortises 108b are visible on the rear edge of the body pad 102. As those of ordinary skill in the art can appreciate, a pocket or other receptacle suitable to receive the respective tenon of the back pad 104 may be used similar to the mortise.

Figure 5:
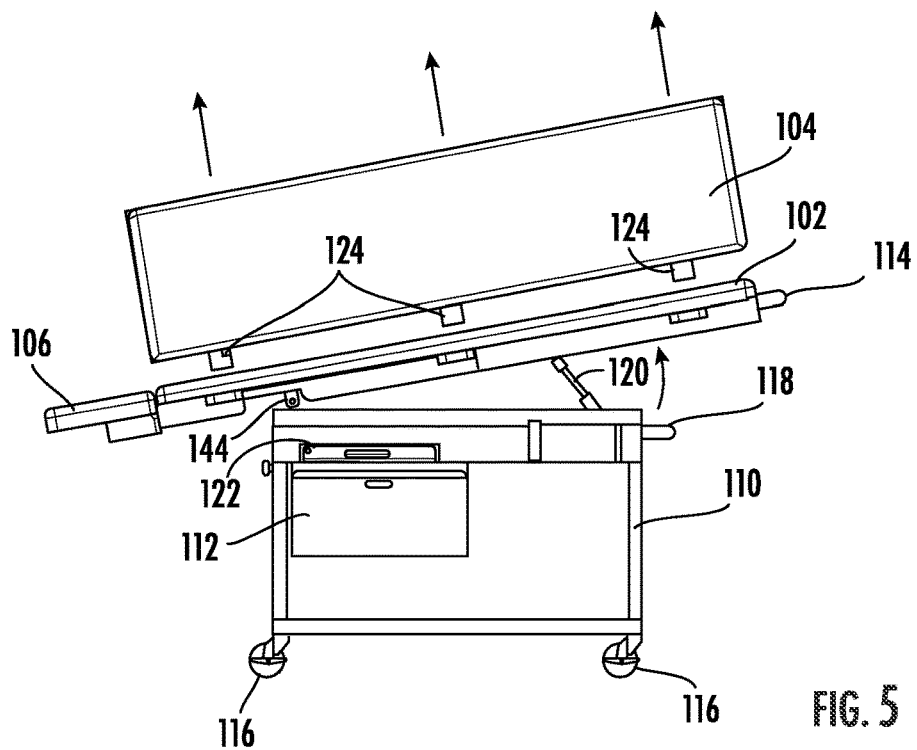
FIG. 5 is a front view of the adjustable hospital bed with a body pad tilted up on one end and the back pod being removed.
Figure 6:
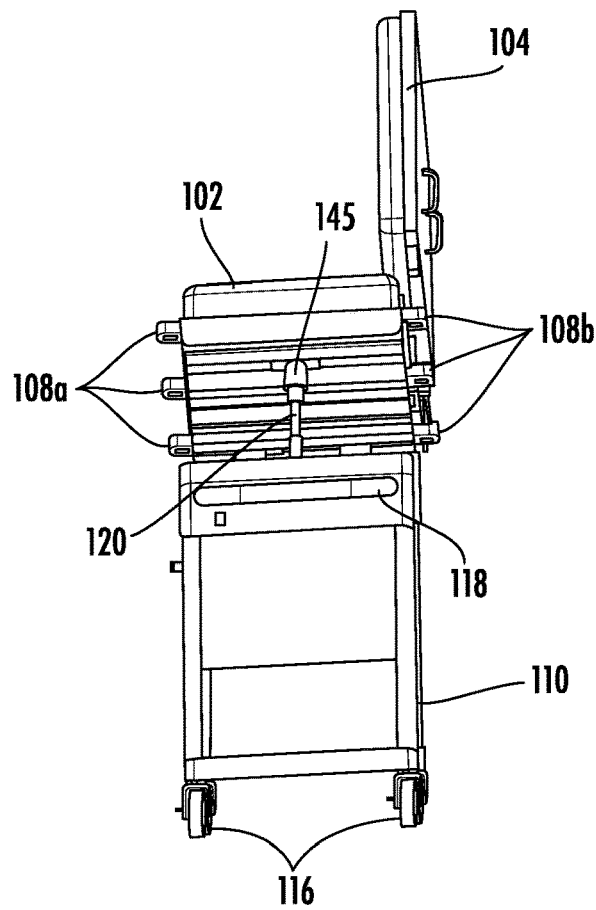
FIG. 6 is a right side view of the adjustable hospital bed with the body pad tilted up on one end as shown in FIG. 5.

Referring now to FIGS. 5 and 6, the back pad 104 is shown removed from the body pad 102 so that the tenons 124 of the back pad 104 are visible. Also, an important feature of the bed 100 is the ability to tilt the head end of the body pad 102 upwards as shown in FIGS. 5 and 6. This elevates the head and upper body of the patient as desired.

A linear actuator 120 has a first end coupled to the support cart 110 and a second end coupled to the underside of the body pad 102 proximate the head end via a head end ball joint 145. Accordingly, as the liner actuator 120 extends, the head end of the body pad 102 raises upwards. A foot end ball joint 144 is secured to the support frame 110 and the underside of the body pad 102 proximate the foot end. The foot end ball joint 144 allows the body pad 102 to rotate about it when the linear actuator 120 is raising or lowering the body pad 102.

Figure 7A:
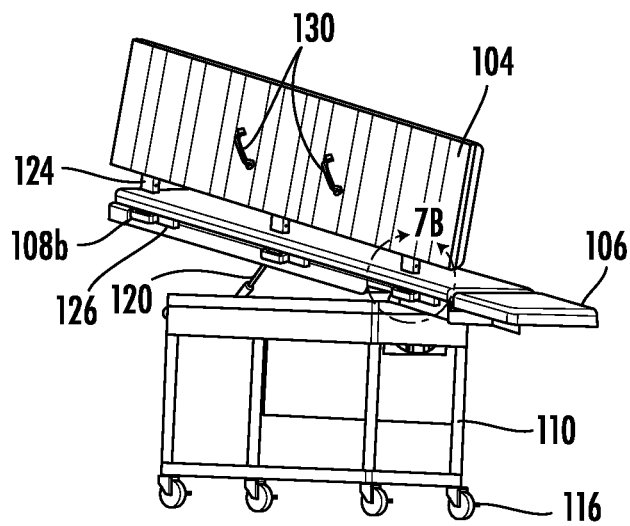
FIG. 7A is a rear view of the of the adjustable hospital bed with the body pad tilted up on one end as shown in FIG. 5.
Figure 7B:
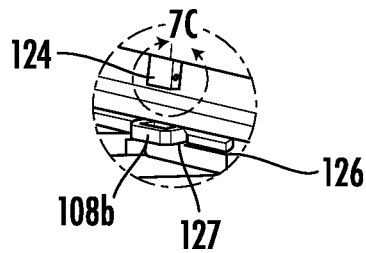
FIG. 7B is a detail view of FIG. 7A illustrating a back pad tendon and a back pad locking rod used to secure the back pad to the body pad.
Figure 7C:
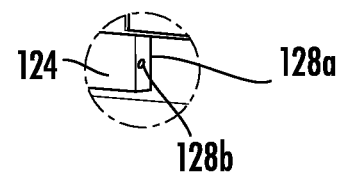
FIG. 7C is a detail view of FIG. 7B illustrating alignment holes of the back pad tendon configured to adjust an angle of the back pad relative to the body pad.

Referring now to FIGS. 7A, 7B, and 7C, another important feature of the bed 100 is the ability to tilt the back pad 104 relative to the body pad 102. Accordingly, the back pad 104 can be perpendicular to the body pad 102 or it can be tilted away from the body pad 102. This is accomplished using alignment holes 128 through the plurality of tenons 124 and a back pad locking rod 126. In addition, a rear surface of the back pad 104 may have at least one back pad handle 130 secured thereto.

First, referring to FIG. 78, the back pad locking rod 126 is shown in the detail view passing through the mortise 108b. Although the tenon 124 has been pulled up from the mortise 108b, once the tenon 124 is seated within the respective mortise 108b, the back pad locking rod 126 is inserted therethrough to prevent the tenon 124 from inadvertently being pulled from the mortise 108b.

Referring now to FIG. 7C, the alignment holes 128a, 128b are illustrated. The alignment holes 128a, 128b are positioned similarly on each of the tenons 124 so that the back pad locking rod 126, which is rigid and linear, can pass through the desired set of alignment holes 128a, 128b. Each set of alignment holes comprises the alignment hole 128a or 128b on each tenon 124 that is positioned the same. Thus, FIG. 7C is representative of two sets of alignment holes 128a, 128b. Accordingly, if the back pad 104 is to be positioned perpendicular, the first set of alignment holes 126a is aligned with the apertures 127 on each mortise 108b. If the back pad 104 is desired to be tilted back from the body pad 102, then the second set of alignment holes 126b is aligned with the apertures 127 on each mortise 108a.

Figure 8:
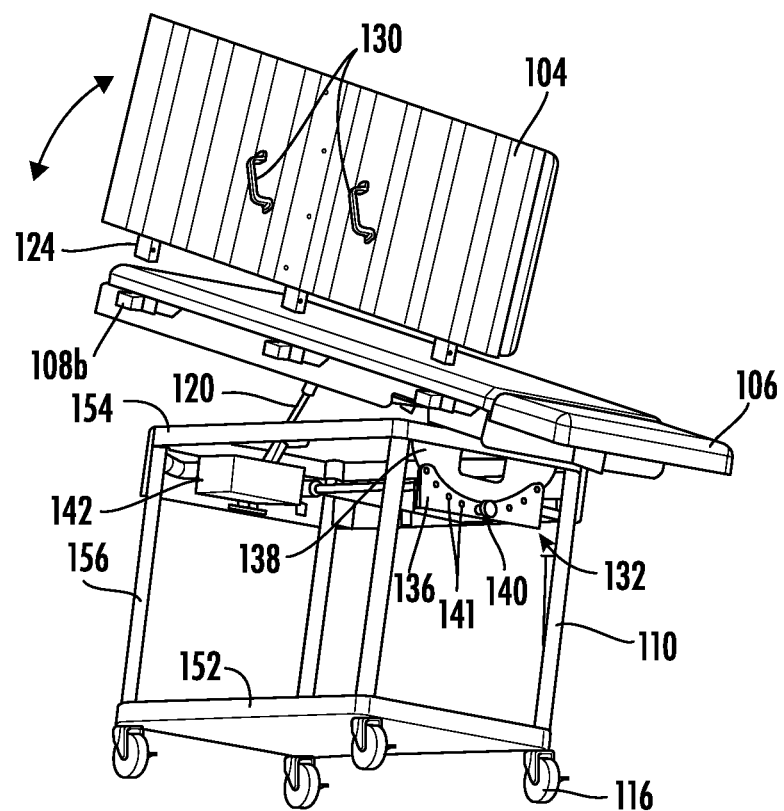
FIG. 8 is a left side perspective view of the adjustable bed illustrating a tilt adjustment mechanism configured to adjust titling of the body pad to the front and rear of the support frame.

The body pad 102 also the ability to be tilted laterally relative to the support frame 110 using a tilt adjustment mechanism 132 as illustrated in FIG. 8. The support frame 110 may have a power supply 142 in electrical communication with the linear actuator 120.

In addition, the support frame 110 includes a lower platform 152, an upper platform 154, and a plurality of vertical supports 156 therebetween. The tilt adjustment mechanism 132 includes a first portion 136 secured to the top end of the support frame 110 and a second overlapping portion 138 in communication with an underside of the body pad 102. The second overlapping portion 138 of the tilt adjustment mechanism 132 is configured to rotate relative to the first portion 136 to laterally tilt the body pad 102 relative to a front or rear of the support frame 110. The tilt adjustment mechanism 132 includes a handle 140 and a plurality of adjustment holes 141 cooperating to secure the body pad 102 at a desired tilting angle relative to the support frame 110.

Accordingly, it is important the head end ball joint 145 that is coupled to the linear actuator 120 and the foot end ball joint 144 are both configured to account for movement in all directions as the body pad 102 is tilted up and down, and also laterally. As those of ordinary skill in the art can appreciate, other types or combinations of connections may be used to accommodate movement other than the ball joints that are provided here as examples in one aspect.

Figure 9:
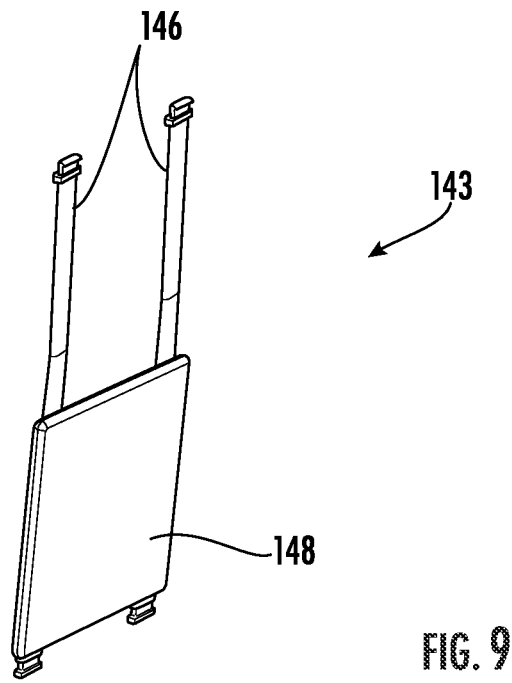
FIG. 9 is a harness of the adjustable hospital bed that fits around the patient to secure them on their side against the back pad.
Figure 10:
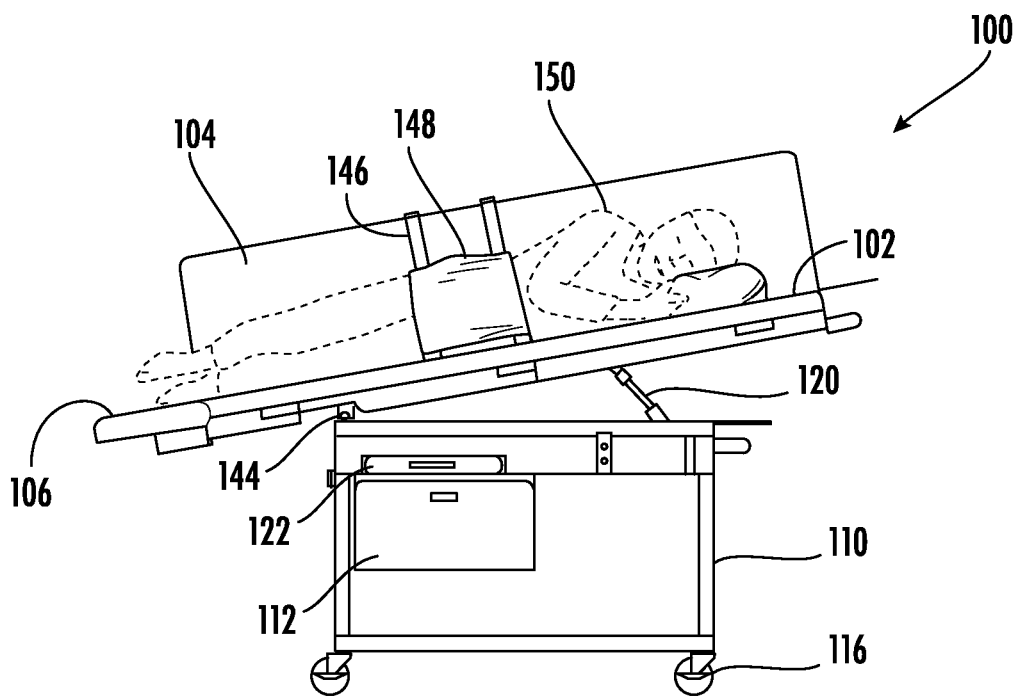
FIG. 10 is a schematic illustrating a patient secured on their side using the adjustable hospital bed of the present invention.

In order to secure the patient to the bed 100 a removable harness 143 comprising a torso pad 148 and at least one strap 146 is provided as illustrated in FIG. 9. The torso pad 148 is configured to be placed adjacent to a torso of the patient and the at least one strap 146 slides around the back pad 104 and body pad 102 to secure the patient 150 laterally on their side against the back pad 104 as shown in FIG. 10.

Accordingly, a method of laterally positioning the patient 150 using the adjustable hospital bed 100 described above includes positioning the patient 150 on the body pad 102 on their side. The method also includes placing the torso pad 148 adjacent to a torso of the patient 150, sliding the straps 146 that are attached to the torso pad 148 around the back pad 104 and body pad 102 to secure the patient 150 laterally on their side against the back pad 104. In addition, the method includes using the linear actuator 120 and the tilt adjustment mechanism 132 to secure the patient 150 at the desired lateral position.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An adjustable hospital bed for laterally positioning a patient comprising:
    a support frame having a top end and a bottom end;
    a plurality of wheels secured to the bottom end of the support frame;
    a body pad having a head end and a foot end, and a plurality of back pad mortises around a periphery of the body pad, the body pad adjustably secured to the top end of the support frame; and
    a back pad having a top edge, a bottom edge, and a plurality of back pad tenons extending from the bottom edge and removably inserted into the plurality of back pad mortises of the body pad to support the back pad on the bottom edge at an angle relative to the body pad;
    a tilt adjustment mechanism having a first portion secured to the top end of the support frame and a second overlapping portion in communication with an underside of the body pad, wherein the second overlapping portion of the tilt adjustment mechanism is configured to rotate relative to the first portion to laterally tilt the body pad relative to a front or rear of the support frame.

2. The adjustable hospital bed of claim 1, further comprising a linear actuator having a first end secured to the top end of the support frame and a second end secured to an underside of the body pad, the linear actuator configured to lift the head end of the body pad.

3. The adjustable hospital bed of claim 1, wherein the tilt adjustment mechanism having a handle and a plurality of adjustment holes cooperating to secure the body pad at a desired tilting angle relative to the support frame.

4. The adjustable hospital bed of claim 1, further comprising an upper push handle and a lower push handle, wherein the upper push handle is secured to the body pad, and the lower push handle is secured to the support frame.

5. The adjustable hospital bed of claim 1, wherein a rear surface of the back pad comprises at least one back pad handle secured thereto.

6. The adjustable hospital bed of claim 1, further comprising a foot pad extending from the foot end of the body pad, wherein the foot pad is configured to be rotated up and locked in alignment with the body pad or unlocked and rotated down.

7. The adjustable hospital bed of claim 1, further comprising a removable harness comprising a torso pad and at least one strap, wherein the torso pad is configured to be placed adjacent to a torso of the patient and the at least one strap slides around the back pad and body pad to secure the patient laterally on the patients side against the back pad.

8. The adjustable hospital bed of claim 2, wherein the support frame further comprising a power supply in electrical communication with the linear actuator.

9. The adjustable hospital bed of claim 1, wherein the support frame comprises a lower platform, an upper platform, and a plurality of vertical supports therebetween.

10. The adjustable hospital bed of claim 1, further comprising a back pad locking rod configured to removably secure the back pad tenons to the back pad mortises by sliding the back pad locking rod therethrough.

11. The adjustable hospital bed of claim 10, wherein the plurality of back pad tenons comprise a plurality of position apertures configured to receive the back pad locking rod therethrough and to secure the back pad at a desired angle relative to the body pad.

12. An adjustable hospital bed for laterally positioning a patient comprising:
    a support frame having a top end and a bottom end;
    a body pad having a head end and a foot end, and a plurality of back pad mortises around a periphery of the body pad, the body pad adjustably secured to the top end of the support frame;
    a back pad having a top edge, a bottom edge, and a plurality of back pad tenons extending from the bottom edge and removably inserted into the plurality of back pad mortises of the body pad to support the back pad on the bottom edge at an angle relative to the body pad;
    a linear actuator having a first end secured to the top end of the support frame and a second end secured to an underside of the body pad, the linear actuator configured to lift the head end of the body pad; and
    a tilt adjustment mechanism having a first portion secured to the top end of the support frame and a second overlapping portion in communication with an underside of the body pad, wherein the second overlapping portion of the tilt adjustment mechanism is configured to rotate relative to the first portion to laterally tilt the body pad relative to a front or rear of the support frame.

13. The adjustable hospital bed of claim 12, wherein the tilt adjustment mechanism having a handle and a plurality of adjustment holes cooperating to secure the body pad at a desired tilting angle relative to the support frame.

14. The adjustable hospital bed of claim 12, wherein a rear surface of the back pad comprises at least one back pad handle secured thereto.

15. The adjustable hospital bed of claim 12, further comprising a foot pad extending from the foot end of the body pad, wherein the foot pad is configured to be rotated up and locked in alignment with the body pad or unlocked and rotated down.

16. The adjustable hospital bed of claim 12, further comprising a removable harness comprising a torso pad and at least one strap, wherein the torso pad is configured to be placed adjacent to a torso of the patient and the at least one strap slides around the back pad and body pad to secure the patient laterally on the patients side against the back pad.

17. The adjustable hospital bed of claim 12, further comprising a back pad locking rod configured to removable secure the back pad tenons to the back pad mortises by sliding the back pad locking rod therethrough, wherein the plurality of back pad tenons comprise a plurality of position apertures configured to receive the back pad locking rod therethrough and to secure the back pad at a desired angle relative to the body pad.

18. A method of laterally positioning a patient using an adjustable hospital bed comprising a support frame having a top end and a bottom end, a body pad having a head end and a foot end and a plurality of back pad mortises around a periphery of the body pad, the body pad adjustably secured to the top end of the support frame, a back pad having a plurality of back pad tenons extending from a bottom edge and removably inserted into the plurality of back pad mortises of the body pad to support the back pad on the bottom edge at an angle relative to the body pad, a linear actuator having a first end secured to the top end of the support frame and a second end secured to an underside of the body pad, and a tilt adjustment mechanism configured to rotate to laterally tilt the body pad relative to a front or rear of the support frame, a tilt adjustment mechanism having a first portion secured to the top end of the support frame and a second overlapping portion in communication with an underside of the body pad, wherein the second overlapping portion of the tilt adjustment mechanism is configured to rotate relative to the first portion to laterally tilt the body pad relative to a front or rear of the support frame, the method comprising: positioning the patient on the body pad on the patients; placing a torso pad adjacent to a torso of the patient; sliding a strap that is attached to the torso pad around the back pad and body pad to secure the patient laterally on their side against the back pad; and using the linear actuator and the tilt adjustment mechanism to secure the patient at a desired lateral position.

* * * * *